(12) United States Patent  (10) Patent No.: US 6,620,184 B2
de Laforcade et al.  (45) Date of Patent: Sep. 16, 2003

(54) RELEASE MECHANISM FOR GRASPING DEVICE

(75) Inventors: Hughes I. de Laforcade, Manchester, MA (US); Henri F. de Guillebok, Manchester, MA (US)

(73) Assignee: Microline Inc., Beverly, MA (US)

( * ) Notice: Subject to any disclaimer, the term of this patent is extended or adjusted under 35 U.S.C. 154(b) by 163 days.

(21) Appl. No.: 09/795,808

(22) Filed: Feb. 28, 2001

(65) Prior Publication Data

US 2002/0120289 A1 Aug. 29, 2002

(51) Int. Cl.⁷ .............................................. A61B 17/28

(52) U.S. Cl. ...................................... 606/205; 606/207

(58) Field of Search ................................ 606/170, 171, 606/205, 206, 207, 208; 81/304, 306, 318, 319, 320, 324, 369, 329, 331, 338, 339, 340, 341

(56) References Cited

U.S. PATENT DOCUMENTS

| | | | | |
|---|---|---|---|---|
| 5,174,300 A | * | 12/1992 | Bales et al. | 294/19.1 |
| 5,483,952 A | * | 1/1996 | Aranyi | 600/131 |
| 5,626,608 A | * | 5/1997 | Cuny et al. | 600/131 |
| 5,951,577 A | * | 9/1999 | Mayenberger et al. | 606/159 |

* cited by examiner

Primary Examiner—Michael J. Milano
Assistant Examiner—Vy Q. Bui
(74) Attorney, Agent, or Firm—Don Halgren

(57) ABSTRACT

A ratchet release mechanism for a medical device. The release mechanism permits both a smooth and a stepped actuation of a grasper on a distal end of the medial device. The medical device has a fixed handle and a movable handle. The release mechanism comprises an elongated toothed plate arrangement supported in a release housing and an elongated smooth plate arranged adjacent the toothed plate arrangement in the release housing. The release housing is pivotably supported between the handles to permit the handles to move in a stepped or a smooth manner to effect actuation of the grasper.

15 Claims, 4 Drawing Sheets

RELEASE MECHANISM FOR GRASPING DEVICE

BACKGROUND OF THE INVENTION

1. Field of the Invention

This invention relates to handle assemblies for manipulable surgical devices, and more particularly to release mechanisms within that handle assembly.

2. Prior Art

Laparoscopic surgery may be defined as minimally invasive surgery upon a patient, utilizing small or miniaturized medical devices by which body tissue is cut, removed or cauterized by small manipulable devices through small incisions or openings within the patient's body.

One device needed for such surgery may be characterized as a grasper or dissector. Such a device may be utilized to grab, dissect, treat or move tissue out of the surgical situs where other tissue may be surgically treated.

There exists a need for a device which will permit ready manipulation of tissue of any particular size or thickness encountered which can be grasped and maintained or manipulated readily by a single hand of an operating surgeon, and which protects the surgeon from high voltage electricity when cauterizing a patient.

It is therefore an object of the present invention, to provide a grasper or dissector handle arrangement which improves upon the prior art.

It is a further object of the present invention, to provide a handle mechanism of a grasper or dissector device which permits maintaining or manipulating body tissue of any thickness encountered, by use of a simple release mechanism in the handle of the device.

It is yet a further object of the present invention, to provide a release mechanism which permits that medical grasper device to be multi-funtional, to maintain and/or to immediately release a grasping or treatment configuration to that medical device and to provide electrical high voltage insulation when cautery is applied to the handpiece device.

It is still yet a further object of the present invention to provide a handle release mechanism for a grasper device which is very simple to operate and inexpensive to manufacture so as to provide optimum economic conditions for the medical community.

BRIEF SUMMARY OF THE INVENTION

The present invention relates to a handle assembly release mechanism for an elongated medical device such as a laparoscopic grasper or dissector. The handle assembly comprises an elongated frame element having a barrel housing at a first or uppermost end thereof, a cautery pin and elongated ring portion at a second or lowermost portion thereof for receipt of the operator's fingers. The barrel housing is arranged to receive the proximal end of an elongated outer shaft of the grasper or dissector device. The elongated shaft of that grasper device has a distal end at which a pair of forceps are pivotably disposed. The forceps device at the distal end of the elongated shaft are opened and closed in a known manner by reciprocal movement of an inner shaft. The inner shaft has a proximal end that extends through the barrel housing and is in pivotable attachment with a movable handle member. The movable handle member pivots about a rear pivot pin in a rear pin opening in the frame of the fixed handle assembly.

A ratchet point is arranged at a mid-location of the elongated frame portion of the fixed handle assembly, and a biasing spring is arranged in that fixed handle assembly thereadjacent.

The release mechanism is arranged between the movable handle and the fixed handle. The release mechanism comprises a housing defined by a pair of elongated parallel plates. The elongated parallel plates have a bridging portion joining them therebetween. The release mechanism is attached at its rearmost end by the rear pin, to the rear pin hole in the movable handle. The release mechanism is pivotable about that rear pin.

A plurality of elongated arcuately-shaped toothed plates are disposed between the side members of the release mechanism. The plurality of arcuately shaped plates is comprised of a main toothed plate and several arcuately-shaped toothed sub-plates. The toothed plates have a first or forward end and a second or rear end. The main tooth plate has a rear pin hole at its rearward most end. The rear pin which extends through a release mechanism housing extends also through the rear pin hole of the main toothed plate. The forward end of the main toothed plate has a forward pin hole therethrough. A forward pin is disposed through the forward pin hole of the main toothed plate and is received in a pair of holes in the forward end of the release mechanism housing.

An elongated arcuately-shaped smooth plate is arranged adjacent the plurality of toothed elongated plates within the release mechanism housing. The elongated smooth plate has a first or forward end and a second or a rear end. The rear end of the arcuately-shaped smooth plate has a rear pin hole therethrough. The rear pin of the tooth plates and the release mechanism housing also passes through the rear end hole of the smooth plate.

The main toothed plate and the sub-plates with teeth, have an elongated slot extending in a generally forwardly to rearwardly direction.

The slot in the toothed plates has a first or forward end and a second or rearward end.

The smooth elongated plate has an elongated slot at its forwardmost end. The smooth plate is arranged to be pivotally juxtaposed adjacent the array of toothed plates. The smooth plate has its slot arranged at an angle with respect to the slot of the toothed plates. The slot in the smooth plate has a first end which is in alignment with the slot in the first or forward end of the toothed plates.

A pair of released buttons are arranged on each side of the pair of parallel plates defining the housing of the release mechanism. The release buttons are connected by a button pin extending therebetween. The button pin also extends through the slot in the toothed plate assembly as well as in the slot of the smooth plate.

In operation of the release mechanism of the present invention the operating surgeon would have fingers arranged through the fixed handle and the movable handle. Respective arcuate movement of the pivotable or movable handle towards the fixed handle would cause the inner shaft attached to the distalmost end of the movable handle to be pulled rearwardly and thus effect the closing of the forceps on the distalmost end of the grasper device. When the release button is in its rearwardmost position, with its connecting pin within the rearwardmost location of the slot within the release mechanism housing and also in the rearwardmost position in the slot of the toothed plate assembly and the slot in the smooth plate, movement of the movable handle with respect to the fixed handle is unhindered, thus permitting the surgeon to open and close the forceps of the medical device, at will. This is permitted by virtue of the smooth plate being pivoted upwardly about the rear pin, to a location where the upper edge of the smooth plate is disposed above the teeth in the toothed plate assembly. In that manner, the ratchet point in the framed portion of the fixed handle assembly is not permitted to engage the teeth within the toothed plate assembly.

When the movable handle member is pulled rearwardly and the release button arrangement is pushed forwardly in its slot within the release mechanism housing, the release button connecting pin is pushed forward in the slot of the toothed plate assembly as well as in the slot for the smooth plate. The smooth plate is thus cammed downwardly and pivoted about its rearwardmost pivot pin and pin hole due to the camming action of the release button pin in the slot therein. Thus the teeth in the main toothed plate and attached toothed sub-plates are exposed to the ratchet point in the fixed handle assembly, and those toothed plates are biased theretoward by the leap spring within the fixed handle assembly.

The attending surgeon may thus squeeze the movable handle towards the fixed handle thus ratcheting downwardly on the handle assembly. This permits the forceps to be closed in a stepwise manner. A body tissue may be grasped firmly within those forceps and held there by the ratchet point engaging any of the series of teeth within the elongated toothed plates.

Prompt release of the forceps from the tissue is effected by a downward pressure on the trigger-like bridging portion of the release mechanism housing. This downward pressure on the bridging portion of the released mechanism housing pushes the leaf spring downwardly and permits the movable handle to be displaced away from the fixed handle thus permitting the opening the forceps and permitting release of the body tissue from therebetween.

It is thus to be noted, that the unique release mechanism permits a wide range of angular openings of the forceps, to permit a locking thereat, thus enabling the operating physician to grasp almost any size body tissue thereby. The simple release of this mechanism, being effected by a trigger-like pull on the bridging portion of the release mechanism housing thus overides the engagement of the ratchet point with the teeth on the toothed plates, permitting a fast and responsive release of the tissue and actuating the grasper mechanism for a subsequent grasping operation.

The invention thus comprises a ratchet release mechanism for a medical device permitting a smooth and a stepped actuation of a grasper on a distal end of the medial device. The medical device has a fixed handle and a movable handle. The release mechanism comprises an elongated toothed plate arrangement supported in a release housing. An elongated smooth plate is arranged adjacent the toothed plate arrangement in the release housing. The release housing is pivotably supported between the handles to permit the handles to move in a stepped or a smooth manner to effect actuation of the grasper. The elongated plates are disposed about a common pivot pin. The release housing includes a slot with a pin extending therethrough, wherein movement of the pin effects arcuate displacement of the toothed plate arrangement with respect to the smooth plate. The smooth plate arrangement has a slot therein and the toothed plate arrangement has a slot therein, all of the slots having a commonly aligned forwardmost end. The fixed handle has a ratchet point thereon which is engageable with the toothed plate arrangement. The toothed plate arrangement is fixedly supported in the release housing. The smooth plate arrangement is pivotably supported in the release housing. The release housing is pivotably supported on the movable handle. A leaf spring is attached to the fixed handle to bias the toothed plate assembly in the release housing against the pivot point. The release housing has a bridging portion which is pressable to displace the toothed plate arrangement in the release housing out of engagement with the ratchet point, and thus permit smooth action of the grasper.

The invention also comprises a method of stepwise grasping and manipulating a body tissue in a laparoscopic procedure, by an elongated grasping device, said method comprising the steps of: pivoting a plurality of elongated, adjacently disposed arcuate members about a common pivot axis through their rear end thereof, each arcuate member supported in a housing, wherein at least one of the arcuate members has an upper edge with a plurality of teeth thereon, each of the arcuate members having a slot in a forward end thereof; engaging at least one of the arcuate members by a ratchet point in the grasping device to move a grasper jaw arrangement on a distal end of the grasper device to secure a tissue therein; and moving one of the arcuate members with respect to the remainder of the arcuate members to effect release of the arcuate members and unlocking of the grasper jaw arrangement and release of tissue therefrom. The method includes moving a pin transversely through the slots in the forward end of the plurality of arcuate members to effect the moving of the one of the arcuate members with respect to the remainder of the arcuate members thus effecting pivoting movement therebetween. At least one of the arcuate members has a smooth edge and the remainder of the plurality of arcuate members have teeth on a upper edge thereof. The slot in the arcuate member having a smooth upper edge thereon is arranged out of alignment with respect to the slots in the remainder of the arcuate members. The slot in the arcuate member having a smooth upper edge thereon has a rearmost slot portion arranged at an angle with respect to a forward slot portion thereof.

BRIEF DESCRIPTION OF THE DRAWINGS

The objects and advantages of the present invention will be come more apparent when viewed in conjunction with the following drawings, in which.

DESCRIPTION OF THE PREFERRED EMBODIMENTS

Figure 1:
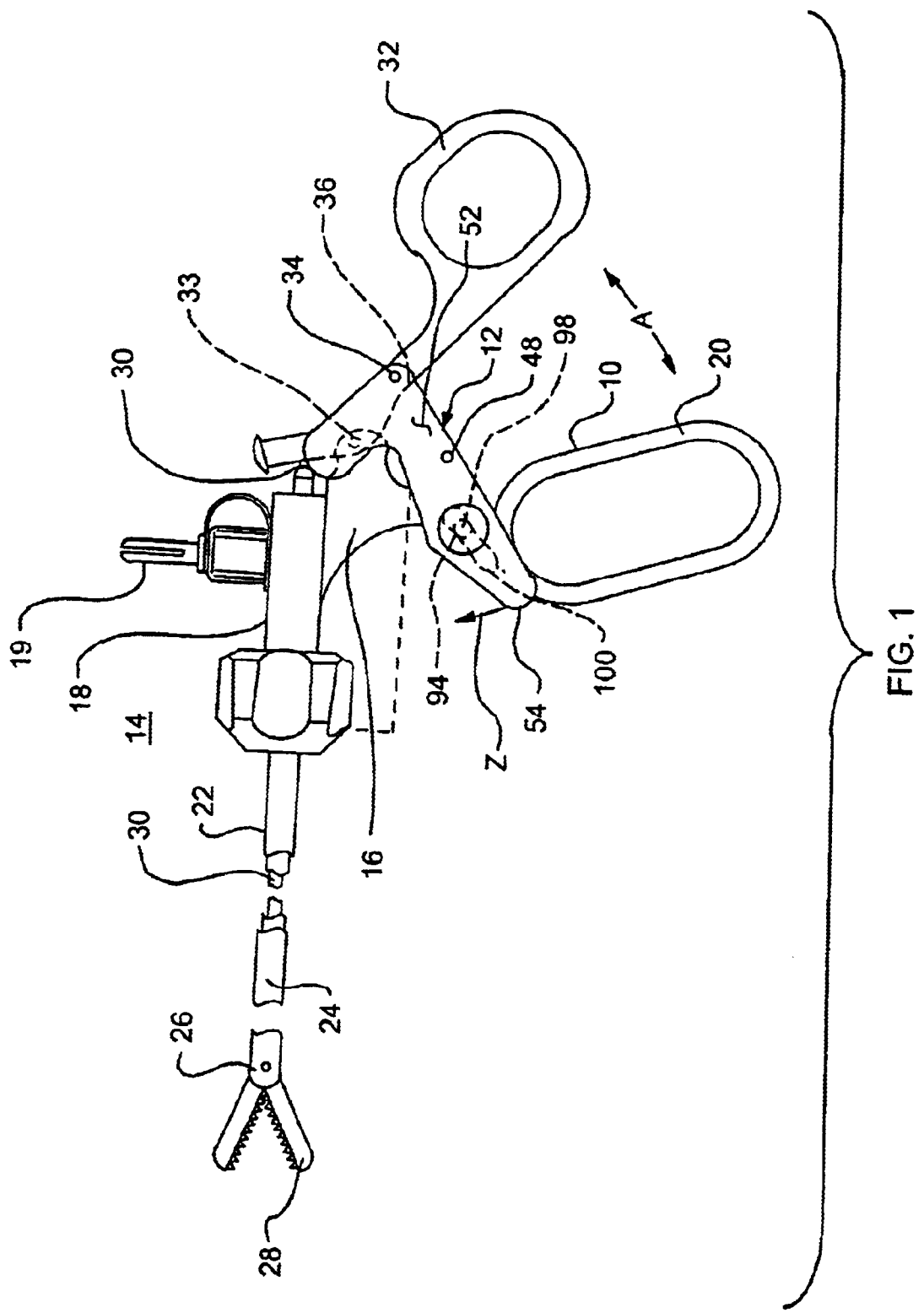
FIG. 1 is a side elevation view of a grasper device constructed according to the principles of the present invention.

Referring now to the drawing in detail, and particularly to FIG. 1, there is shown the present invention which comprises a handle assembly 10 with a release mechanism 12, for an elongated medical device such as a laparoscopic grasper 14 or the like. The handle assembly 10, as may be seen in FIGS. 1 and 4, comprises an elongated frame element 16 having a barrel housing 18 at a first or uppermost end thereof with an insulated dissector-coupled electrical contact 19 thereat. An elongated ring portion 20 is at a second or lowermost portion of the frame 16 for receipt of the surgeon's fingers. The barrel housing 18 is arranged to receive the proximal end 22 of an elongated outer shaft 24 of the grasper device 14. The elongated shaft 24 of that grasper device 14 has a distal end 26 at which a pair of forceps (or dissectors) 28 are pivotably disposed. The forceps device 28 at the distal end 26 of the elongated shaft 24 are opened and closed in a known manner by reciprocal movement of an inner shaft 30. The inner shaft 30 has a proximal end that extends through the barrel housing 18 and is in pivotable attachment with an upper end of an elongated movable handle member 32, as may be seen in FIG. 1. The movable handle member 32 pivots about an upper pivot pin 33 in an upper pin opening 35 in the frame 16 of the fixed handle assembly 10, as shown in FIGS. 1 and 4.

Figure 4:
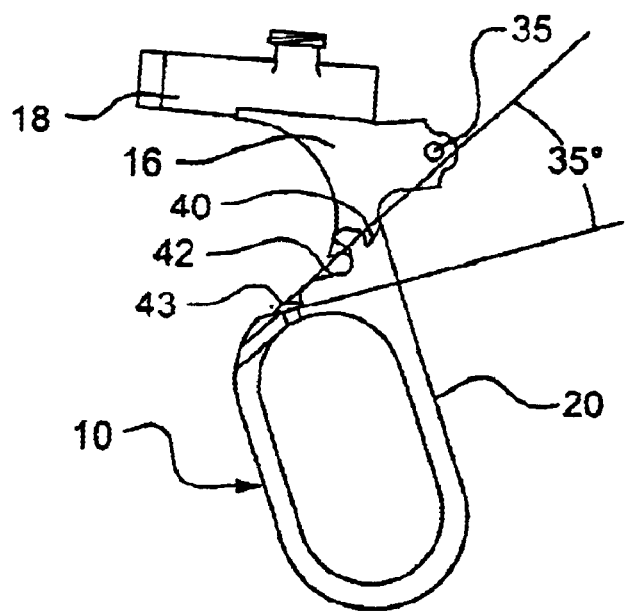
FIG. 4 is a side elevational of the fixed handle assembly of the present invention.

A ratchet point 40 is arranged at a mid-location of the elongated frame portion 16 of the fixed handle assembly 10, and a generally linear biasing spring 42 is securely arranged by a screw 43 in that fixed handle assembly 10 thereadjacent, as is shown in FIG. 4.

The release mechanism 12 is pivotably arranged between the movable handle 32 and the fixed handle 10, as shown in FIG. 1. The release mechanism 12 comprises a housing 48 defined by a pair of elongated parallel side members or plates 50 and 52, as may be seen in FIGS. 2 and 3. The elongated parallel plates 50 and 52 of the housing 48 have a bridging portion 54 joining them therebetween. The release mechanism 12 is attached at its rearmost end by the rear pin 34, to the rear pin hole 36 in the movable handle 32, as shown in FIG. 1. The release mechanism 12 is pivotable about that rear pin 34, in the direction as indicated by arrow "Z" in FIG. 1.

Figure 2:
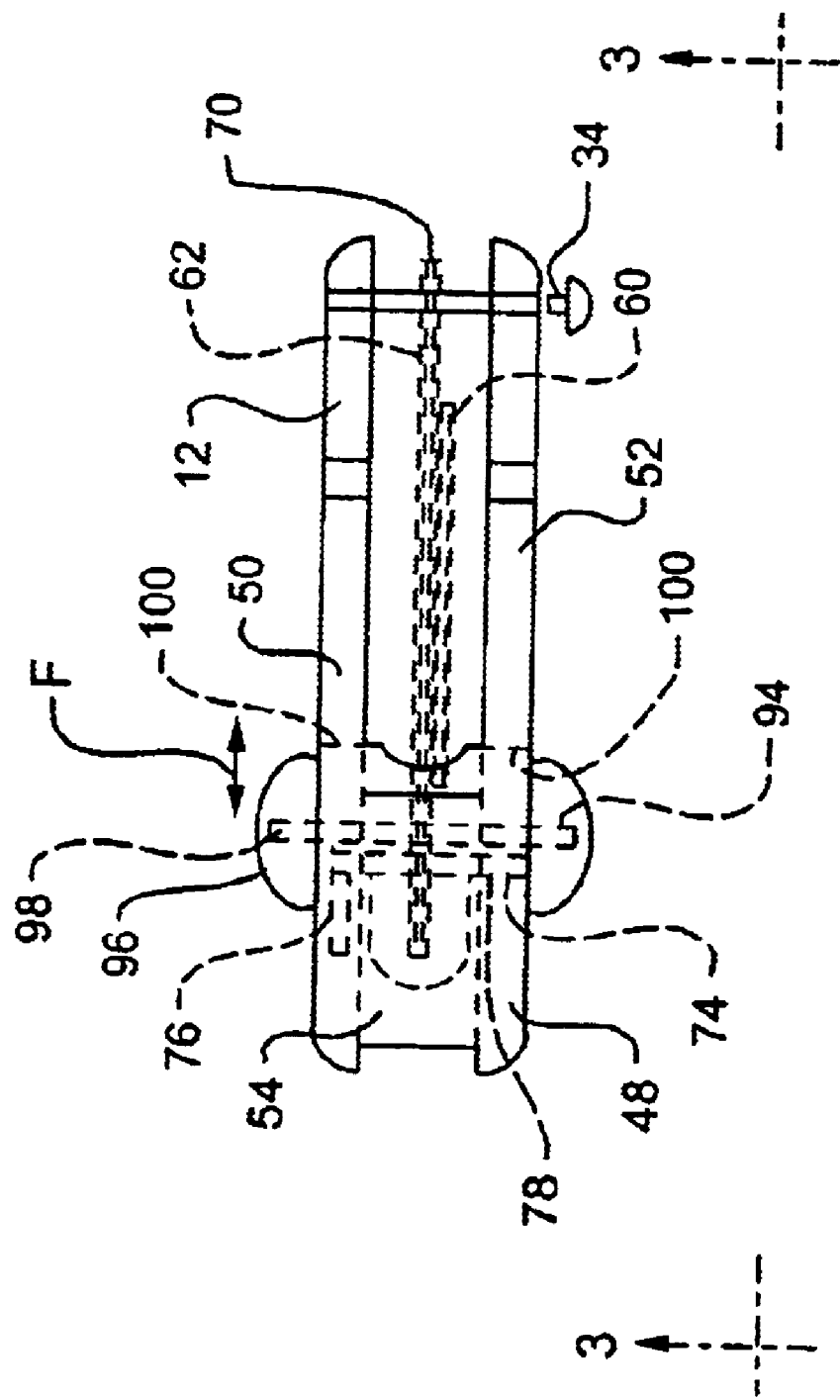
FIG. 2 is a plan view of the release mechanism of the present invention.
Figure 3:
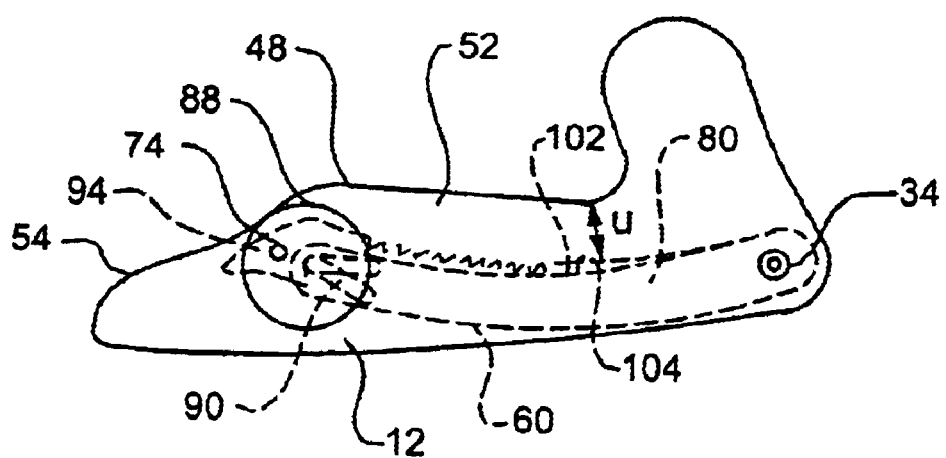
FIG. 3 is a view taken along the: lines 3—3 of FIG. 2.
Figure 5:
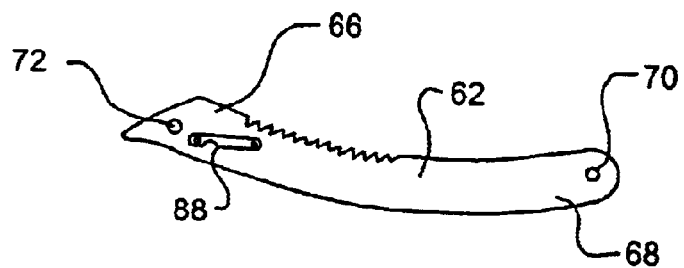
FIG. 5 is a side elevational view of a main toothed plate.
Figure 6:
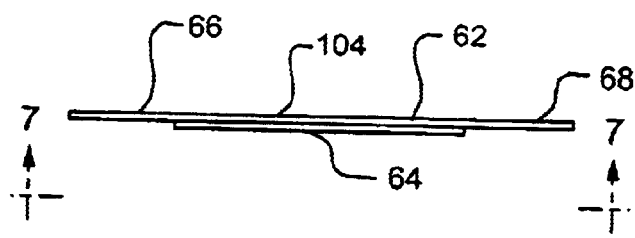
FIG. 6 is a edge view of the main toothed plate shown in FIG. 5 with an attachment of toothed sub-plates thereon.
Figure 7:
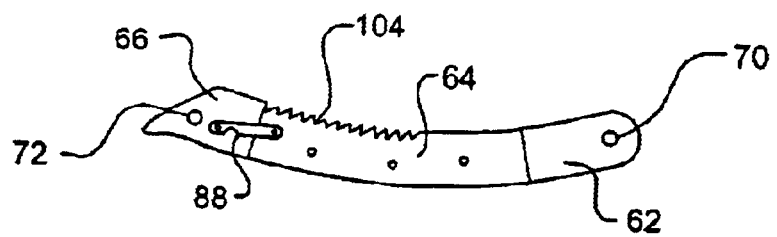
FIG. 7 is a side elevational view of the view shown in FIG. 6.

An elongated, arcuately-shaped toothed plate assembly 60 is disposed between the side members 50 and 52 of the release mechanism 12, as shown in FIGS. 2 and 3. The plate assembly 60 is comprised of an elongated, arcuately-shaped main toothed plate 62, as shown in FIG. 5, and several arcuately-shaped toothed sub-plates 64, as shown in FIGS. 6 and 7. The toothed plates 62 and 64 have a first or forward end 66 and a second or rear end 68. The main toothed plate 62 has a rear pin hole 70 at its rearward most end 68. The rear pin 34 which extends through the release mechanism housing 48 extends also through the rear pin hole 70 of the main toothed plate 62, as may be "visualized" in FIG. 2.

The forward end 66 of the main toothed plate 62 has a forward pin hole 72 therethrough, as shown in FIGS. 5 and 7. A forward pin 74 is disposed through the forward pin hole 72 of the main toothed plate 62 and is received in a pair of holes 76 and 78 in the forward end of the release mechanism housing 48, as may be seen in FIG. 2.

Figure 8:
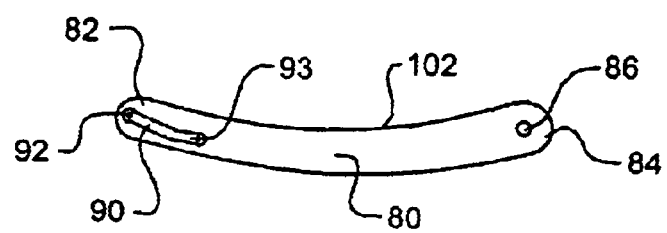
FIG. 8 is a planned view of a smooth plate of the plate assembly portion of the release mechanism.

An elongated, arcuately-shaped smooth plate 80, as may be seen in FIG. 8, is pivotably arranged adjacent the plurality of toothed elongated plates 64 within the release mechanism housing 48. The elongated smooth plate 80 has a first or forward end 82 and a second or rear end 84. The rear end 84 of the arcuately-shaped smooth plate 80 has a rear pin hole 86 therethrough. The rear pin 34 pivotably securing the toothed plate assembly 62 and the release mechanism housing 48 also passes through the rear end 84 hole of the smooth plate 80.

The main toothed plate 62 and the sub-plates 64 with teeth 104, have an elongated slot 88 extending in a generally forwardly to rearwardly direction, as may be seen in FIGS. 3, 5 and 7. The slot 88 in the toothed plate assembly 62 has a first or forward end and a second or rearward end.

The smooth elongated plate 80 has an elongated slot 90 at its forwardmost end 82, as may be seen in FIG. 8. The slot 90 has a rearwardmost end portion 93 which is disposed at a slight angle with respect to the slot 90, as shown in FIG. 8. The smooth plate 80 is arranged to be pivotally juxtaposed adjacent the array of toothed plate assembly 62 about the rear pivot pin 34, as may be seen in FIG. 3. The smooth plate 80 has its slot 90 arranged at an angle with respect to the slot 88 of the toothed plate assembly, as may be seen in FIG. 3. The slot 90 in the smooth plate 80 has a first end 92 which is alignable with the front end of the slot 88 in the first or forward end 66 of the toothed plate assembly 62. The angular relationship of slot 90 with respect to the slot 88 permits the pivotal movement of the smooth plate 80 with respect to the toothed plate assembly 62. The angled portion 93 of the slot 90 permits the smooth plate 80 to stay in its upwardly pivoted position. The smooth plate 80 may be pivoted about pin 34, clockwise (upwardly) as indicated by the arrow "U" shown in FIG. 3, to move the smooth upper edge 102 of the smooth plate 80 into position above the teeth 104 on the toothed plate assembly 60, to thus get the teeth 104 out of engagement with the ratchet point 40 in the frame 16, shown in FIG. 4, when the surgeon wants to keep the ratchet mechanism in its release mode, as described further, hereinbelow.

A pair of released buttons 94 and 96 are arranged on each side of the pair of parallel plates 50 and 52 defining the housing 48 of the release mechanism 12, as may be seen in FIGS. 1, 2 and 3. The release buttons 94 and 96 are connected by a button pin 98 extending therebetween, as shown in FIG. 2. The button pin 98 also extends through the slot 88 in the toothed plate assembly 62 as well as in the slot 90 of the smooth plate 80, as also shown in FIG. 2. Moving the release button 94 and 96 to the right as may be "envisioned" in FIG. 3, would effect the pivoting upwardly (clockwise) of the smooth plate 80 about its pivot pin 34, effecting relative movement between the smooth plate 80 and the toothed plates 62 and 64, thus effecting release of the ratchet engagement therewith. Movement of the buttons 94 and 96 "forwardly" would return the ratcheting action into effect.

In operation of the release mechanism 12 of the present invention the operating surgeon would have fingers arranged through the fixed handle 20 and in the movable handle 36. Respective arcuate movement of the pivotable or movable handle, as represented by arrows "A" in FIG. 1, towards the fixed handle 20 would cause the inner shaft 30 attached to the distalmost end of the movable handle 32 to be pulled rearwardly and thus effect the closing of the forceps 28 on the distalmost end 26 of the grasper device 14. When the release buttons 94 and 96 are in their rearwardmost position, with its connecting pin 98 within the rearwardmost location of the slot 100 within the release mechanism housing 48 and also in the rearwardmost position in the slot 88 of the toothed plate assembly 62 and the slot 90 in the smooth plate 80, movement of the movable handle 32 with respect to the fixed handle 20 is unhindered, thus permitting the physician to open and close the forceps 28 of the medical device 14, at will. This is permitted by virtue of the smooth plate 80 being pivoted upwardly about the rear pin 34, to a location where the upper edge 102 of the smooth plate 80 is disposed above the teeth 104 in the toothed plate assembly 62. In that manner, the ratchet point 40 in the framed portion 16 of the fixed handle 10 is not permitted to engage the teeth 104 within the toothed plate assembly 62.

When the movable handle member 32 is pulled rearwardly and the release button arrangement 94 and 96 is pushed forwardly in its slot 100 within the release mechanism housing 48, as indicated by the arrow "F" in FIG. 2, the release button connecting pin 98 is pushed forward in the slot 88 of the toothed plate assembly 62 as well as in the slot 90 for the smooth plate 80. The smooth plate 80 is thus cammed downwardly (see arrow "U" in FIG. 3) and pivoted about its rearwardmost pivot pin 34 and its pin hole 86 due to the camming action of the release button pin 98 in the slot 90, and out of its "locked" location in the angled slot portion 93 at the rear end of slot 80. Thus the teeth 104 in the main toothed plate assembly 62 (including the attached toothed sub-plates 64) are exposed to the ratchet point 40 in the fixed handle assembly 10, and those toothed plates 62 are biased theretoward by the leap spring 42 within the fixed handle assembly 10, as may be seen in FIG. 4.

The attending surgeon may thus squeeze the movable handle 32 towards the fixed handle 20 thus ratcheting downwardly on the handle release assembly 12. This permits the forceps 28 to be closed in a stepwise manner as per the engagement of the teeth 104 in the toothed plates 62. A body tissue may be thus grasped firmly within those forceps 28 and held there by the ratchet point 40 engaging any of the series of teeth 104 within the elongated toothed plates 62 and 64.

Prompt release of the forceps 28 from the tissue is effected by a downward pressure on the trigger-like bridging portion 54 of the release mechanism housing 12, as may be seen in FIGS. 1, 2 and 3. This downward pressure on the bridging portion 54 of the released mechanism housing 48 pushes the leaf spring 42 downwardly and permits the movable handle 32 to be displaced away from the fixed handle 20 thus permitting the opening the forceps 28 and permitting release of the body tissue from therebetween.

It is thus to be noted, that the unique release mechanism permits a wide range of angular openings of the forceps, to permit a locking thereat, thus enabling the operating physician to grasp almost any size body tissue thereby. The simple release of this mechanism, being effected by a triggerlike pull on the bridging portion 54 of the release mechanism housing 48 thus overides the engagement of the ratchet point 40 with the teeth 104 on the toothed plate assembly 62, permitting a fast and responsive release of the tissue and actuating the grasper mechanism 14 for a subsequent grasping operation.

We claim:

1. A ratchet release mechanism for a medical device permitting a smooth and a stepped actuation of a grasper on a distal end of said medial device, said medical device having a fixed handle and a movable handle, said release mechanism comprising:

an elongated toothed plate arrangement supported in a release housing;

an elongated smooth plate arranged adjacent said toothed plate arrangement in said release housing, said release housing being pivotably supported between said handles to permit said handles to move in a stepped or a smooth manner to effect actuation of said grasper, wherein said release housing includes a slot with a movable pin extending therethrough, wherein movement of said movable pin effects arcuate displacement of said toothed plate arrangement with respect to said smooth plate.

2. The ratchet release mechanism as recited in claim 1, wherein said elongated plates are disposed about a common pivot pin.

3. The ratchet release mechanism as recited in claim 1, wherein said smooth plate arrangement has a slot therein and said toothed plate arrangement has a slot therein, said slots having a commonly aligned forwardmost end.

4. The release mechanism as recited in claim 3, wherein said fixed handle has a ratchet point thereon which is engageable with said toothed plate arrangement.

5. The release mechanism as recited in claim 3, wherein said toothed plate arrangement is fixedly supported in said release housing.

6. The release mechanism as recited in claim 5, wherein said smooth plate arrangement is pivotably supported in said release housing.

7. The release mechanism as recited 2, wherein said release housing is pivotably supported on said movable handle.

8. The release mechanism as recited in claim 7, including a leaf spring attached to said fixed handle to bias said toothed plate assembly in said release housing against said pivot pin.

9. The release mechanism as recited in claim 7, wherein said release housing has a bridging portion which is pressable to displace said toothed plate arrangement in said release housing out of engagement with said ratchet point, and thus permit smooth action of said grasper.

10. A ratchet release mechanism for a medical device permitting a smooth and a stepped actuation of a grasper on a distal end of said medial device, said medical device having a fixed handle and a movable handle, said release mechanism comprising:

an elongated toothed plate arrangement supported in a release housing;

an elongated smooth plate arranged adjacent said toothed plate arrangement in said release housing, said release housing being pivotably supported between said handles to permit said handles to move in a stepped or a smooth manner to effect actuation of said grasper, said elongated plates are disposed about a common pivot pin, said release housing includes a slot with a pin extending therethrough, wherein movement of said pin effects arcuate displacement of said toothed plate arrangement with respect to said smooth plate, said smooth plate arrangement having a slot therein and said toothed plate arrangement having a slot therein, said slots having a commonly aligned forwardmost end; wherein said fixed handle has a ratchet point thereon which is engageable with said toothed plate arrangement; and wherein said toothed plate arrangement is fixedly supported in said release housing, said smooth plate arrangement being pivotably supported in said release housing, and wherein said release housing is pivotably supported on said movable handle.

11. A method of stepwise grasping and manipulating a body tissue in a laparoscopic procedure, by an elongated grasping device, said method comprising the steps of:

pivoting a plurality of elongated, adjacently disposed arcuate members about a common pivot axis through their rear end thereof, each arcuate member supported in a housing, wherein at least one of said arcuate members has an upper edge with a plurality of teeth thereon, and each of said arcuate members having a slot in a forward end thereof;

engaging at least one of said arcuate members by a ratchet point in said grasping device to move a grasper jaw arrangement on a distal end of said grasper device to secure a tissue therein; and moving one of said arcuate members with respect to the remainder of said arcuate members to effect release of said at least one of said arcuate members and unlocking of said grasper jaw arrangement and release of tissue therefrom.

12. The method as recited in claim 11, including the step of:

moving a pin transversely through said slots in said forward end of said plurality of arcuate members to effect said moving of said at least one of said arcuate members with respect to the remainder of said arcuate members thus effecting pivoting movement therebetween.

13. The m et hod as recited in claim 12, where in at least one of said arcuate members has a smooth edge and the remainder of said plurality of arcuate members have said teeth thereon.

14. The method as recited in claim 13, wherein said slot in said arcuate member having a smooth upper edge thereon is arranged out of alignment with respect to said slots in the remainder of said arcuate members.

15. The method as recited in claim 14, wherein said slot in said arcuate member having a smooth upper edge thereon has a rearmost portion arranged at an angle with respect to a forward portion thereof.

* * * * *